United States Patent [19]

Magnussen, Jr.

[11] E Re. 31,586

[45] Reissued May 15, 1984

[54] LIQUID CHROMATOGRAPHY PUMP

[75] Inventor: Haakon T. Magnussen, Jr., Pinole, Calif.

[73] Assignee: Altex Scientific, Inc., Berkeley, Calif.

[21] Appl. No.: 232,945

[22] Filed: Feb. 9, 1981

Related U.S. Patent Documents

Reissue of:

[64] Patent No.: 4,180,375
Issued: Dec. 25, 1979
Appl. No.: 913,359
Filed: Jun. 7, 1978

U.S. Applications:

[63] Continuation-in-part of Ser. No. 761,433, Jan. 21, 1977, Pat. No. 4,131,393.

[51] Int. Cl.[3] ..... F04B 49/06
[52] U.S. Cl. ..... 417/22
[58] Field of Search ..... 417/18-22, 417/43; 210/198.1, 101

[56] References Cited

U.S. PATENT DOCUMENTS

| | | | |
|---|---|---|---|
| 3,787,882 | 1/1974 | Fillmore | 417/43 |
| 3,847,507 | 12/1974 | Sakiyama | 417/22 |
| 3,855,129 | 12/1974 | Abrahams | 417/38 |
| 3,855,515 | 12/1974 | Hutchins, Jr. | 417/22 |
| 3,917,531 | 11/1975 | Magnussen | 210/198.1 |
| 3,932,067 | 1/1976 | Ball | 417/339 |
| 4,024,864 | 5/1977 | Davies | 417/20 |
| 4,045,343 | 8/1977 | Achener et al. | 210/101 |
| 4,108,574 | 8/1978 | Bartley | 417/20 |
| 4,137,011 | 1/1979 | Rock | 417/22 |

*Primary Examiner*—William L. Freeh
*Attorney, Agent, or Firm*—R. J. Steinmeyer; R. R. Meads; John R. Shewmaker

[57] ABSTRACT

A fluid pump mechanism for delivering a smooth output of fluids to a system utilizing at least one piston in a chamber reciprocative therewithin. The piston has strokes that fill and empty the chamber in conjunction with the action of valve means located at the inlet and outlet of the chamber. Motive means causes reciprocation of the piston within the chamber. Control means is also included for minimizing the time during the piston cycle in which the piston is not emptying the chamber. The invention's scope also encompasses a pressure metering device for a fluid forcing means motivated by an electrical motor.

6 Claims, 9 Drawing Figures

FIG-4
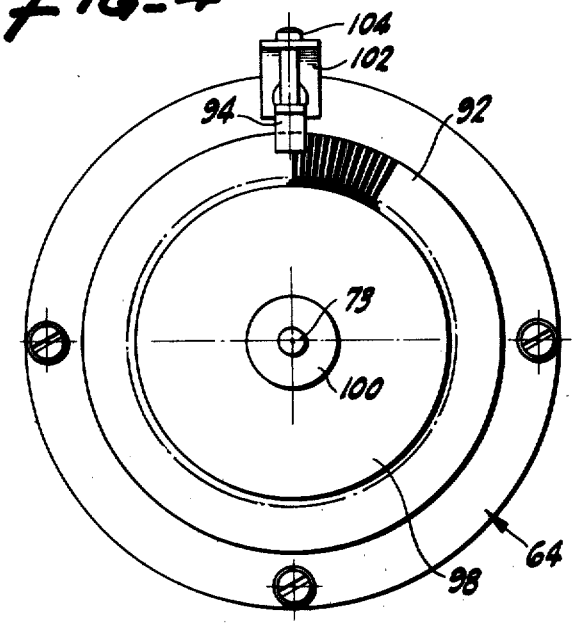
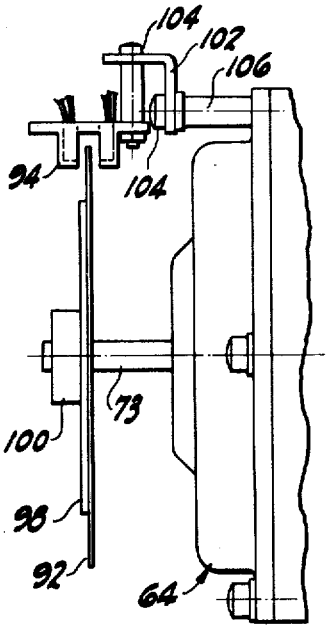
FIG-5
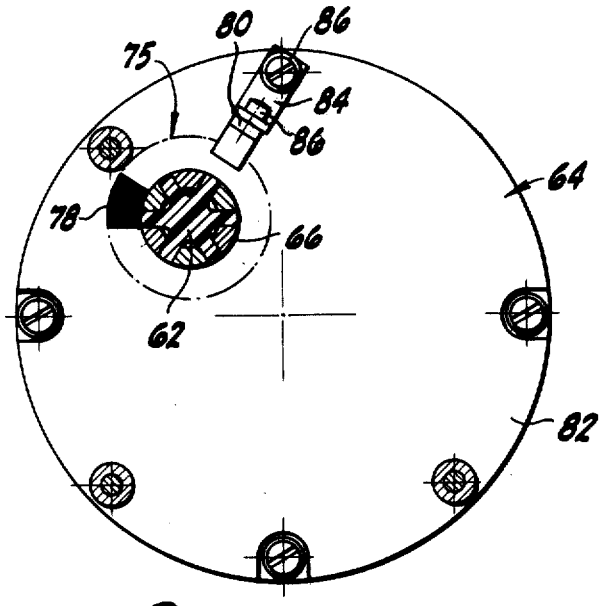
FIG-3

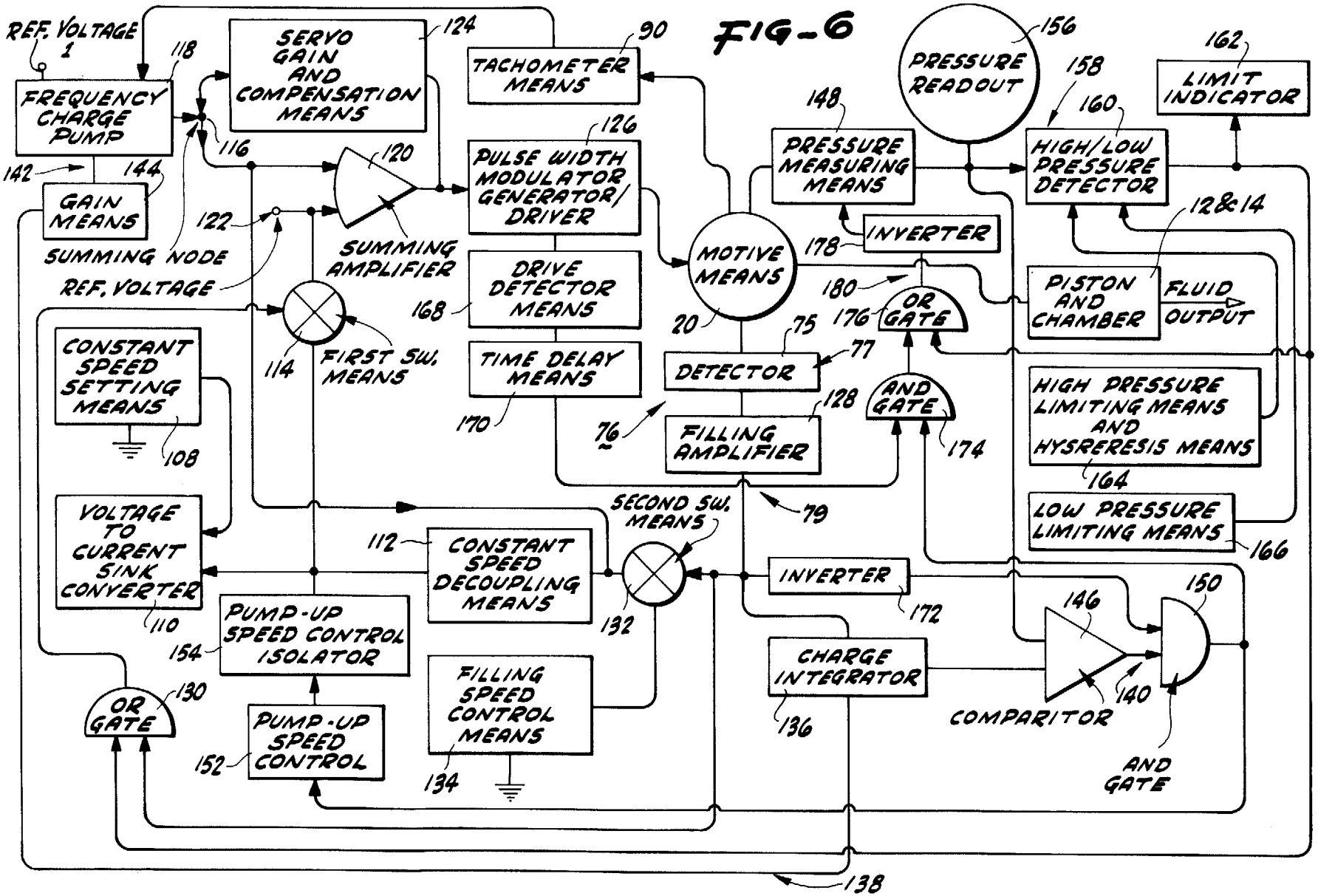
LIMIT INDICATOR
162
128 & 14
HIGH/LOW PRESSURE DETECTOR
160
158
156
PRESSURE READOUT
FLUID OUTPUT
PISTON AND CHAMBER
HIGH PRESSURE LIMITING MEANS AND HYSRERESIS MEANS
164
LOW PRESSURE LIMITING MEANS
166
150
AND GATE
140
146
COMPARITOR
INVERTER
OR GATE
AND GATE
174
172
CHARGE INTEGRATOR
136
138
PRESSURE MEASURING MEANS
148
178
180
176
77
75
128
79
MOTIVE MEANS
20
DETECTOR
FILLING AMPLIFIER
76
SECOND SW. MEANS
132
FIG-6
90
TACHOMETER MEANS
126
PULSE WIDTH MODULATOR GENERATOR/ DRIVER
DRIVE DETECTOR MEANS
168
TIME DELAY MEANS
170
CONSTANT SPEED DECOUPLING MEANS
112
FILLING SPEED CONTROL MEANS
134
124
SERVO GAIN AND COMPENSATION MEANS
120
SUMMING AMPLIFIER
FIRST SW. MEANS
114
PUMP-UP SPEED CONTROL ISOLATOR
154
PUMP-UP SPEED CONTROL
152
116
122
SUMMING NODE
REF. VOLTAGE
118
144
GAIN MEANS
CONSTANT SPEED SETTING MEANS
108
VOLTAGE TO CURRENT SINK CONVERTER
110
130
OR GATE
REF. VOLTAGE 1
FREQUENCY CHARGE PUMP
142

LIQUID CHROMATOGRAPHY PUMP

Matter enclosed in heavy brackets [ ] appears in the original patent but forms no part of this reissue specification; matter printed in italics indicates the additions made by reissue.

CROSS REFERENCES TO RELATED INVENTIONS

The present application is a continuation-in-part of my copending application filed on Jan. 21, 1977, Ser. No. 761,433, now U.S. Pat. No. 4,131,393.

BACKGROUND OF THE INVENTION

The present invention relates to a novel fluid pump mechanism which will deliver fluid or fluids at a given flow rate and with a greatly reduced pulsation. The present invention is particularly useful, although not limited, delivering liquid solvents at very high pressures.

For example, a typical liquid chromatographic column contains packing of finely divided particles for solute separation of a liquid sample. These packed columns create a very high back pressure on the fluid forcing means, i.e.: a positive displacement pump. Moreover, such a pump usually produces a pulsing flow due to the normal action of a piston within a chamber, which can distort the analysis of the solute.

Prior devices have employed pulse dampeners on the output side of the pump as well as dual pistons with overlapping cam methods to overcome such problems. Flow feedback and pressure feedback pumps have been used also. However, these mechanisms work inefficiently and are susceptible to breakdown because of the complexity of the components in their makeup. Such prior pumps still deliver pulsed flow because of chamber compliance compressibility of the fluid being pumped and other factors.

Moreover, constant speed motors driving single piston pumps will produce a pulsing flow and deliver reduced flow rate at high back pressures unless corrected. Additional components such as pressure transducers are expensive and necessarily add to the unreliability of the liquid solvent delivery system.

There is a need for a simple, reliable, metering pump which has greatly reduced pulsations in the delivery of fluids, especially liquid chromatographic solvents.

SUMMARY OF THE INVENTION

In accordance with the present invention a novel fluid pump mechanism is provided.

The mechanism in its basic form includes a piston having a portion reciprocative within a chamber. Valve means permits the filling and emptying of the chamber with the corresponding strokes of the piston. To generate a smooth and relatively pulse free flow of fluid from the mechanism, control means masters the reciprocation of the piston when the chamber is not in the process of emptying or delivering the fluid being pumped. Generally, this would externalize in a speeding up of the piston during its filling stroke and a speeding up of the piston during the "pump-up" period, which is the time when the piston moves to deliver the fluid being pumped, but before the fluid leaves the chamber. Pump-up results from the exertion of back pressure on the chamber outlet, as well as fluid and piston compressibility, seal compliance, and other factors.

Motive means such as, but not limited to an electric motor, drives the piston through its reciprocations within the chamber at a normal or base speed commensurate with the desired flow rate of fluid during the emptying stroke of the piston.

The control means during the filling period may include detection means to acquire and signal the inception of the filling stroke of the piston. Such detection means may take many forms such as a light or photon interception flag rotatable with a shaft actuating a reciprocating means when the motive means includes such elements. A light or photon interceptor module would generate such a signal. Interception of this photon signal would then generate an electrical signal announcing the beginning of the piston filling stroke to filling means which would change the normal speed of the motive means to a speed, usually higher, which would cause filling or refilling of the chamber as quickly as possible. The speed of filling setting would depend on such criteria as check valve response and, degassing or cavitation characteristics of the fluid being pumped. Thus, the pump mechanism completes the filling or refilling phase as quickly as possible so that the piston may devote its greatest effort toward pushing the fluid from the chamber.

Likewise, the detection means may be constructed along the lines of a digital counter having a pulsing tachometer measuring the turning of the motive means shaft. A digital counter would sum these pulses from the pulsing tachometer during the filling period and effect the change of speed of the motive means and piston. Further, the analog equivalent of this digital integration, i.e.: analog integration, may perform the same function.

Where the motive means has reciprocating means, such a format may include a cam shaft, linked to the shaft of the motive means; cam surface; and a cam follower connected to one end of the piston. The detection means would be coordinated with the corresponding portions of the piston cycle devoted the filling of the chamber. After filling, the piston returns to pump the fluid from the newly filled chamber but the flow of fluid delays for a number of reasons. For instance, the back pressure of the body to which the fluid is being pumped, will permit the valve means on the outlet check valve to open only when the back pressure is equaled by the fluid pressure within the chamber. This "pump-up" portion of the cycle also depends on fluid compressibility, seal compliance, and piston and chamber compliance. Under most conditions, the pump-on portion of the piston cycle extends for a finite time during which no fluid passes from the chamber. The mechanism also embraces pump-on means to increase the speed of the motive means immediately after the termination of the chamber filling stroke of the piston and returns the motive means to a predetermined normal speed when the chamber reaches the proper pressure to open the valve means on the chamber outlet. The pump-up means may be mated with the fast filling or fast refilling cycle of the piston heretofore described.

In one aspect, the pump-up means may include a running or variable system to fix the increased speed of the motive means according to the valve of the back pressure encountered. For example, pressure signal means would acquire and transmit the valve of the back pressure to comparitor means. Pump-up gain means would produce a selected reference ramp signal to the comparitor which would step up the motive means for an angular duration ie: a certain number or fraction of turns of the motor shaft. The pump-up gain means might include tachometer means for measuring the axial rotational rate of the motor shaft and transforming the same into a pulse signal. Gain means would receive the puls signal and adjust its amplitude to a certain value. Charge integrator means integrates the amplitude adjusted signal from the gain means and produces a reference ramp signal proportional to the motive means angular duration.

The invention also devises a novel means for deducing the pressure on the motive means if it is an electric motor actuating a fluid forcing means for displacing the fluid against a back pressure. Pressure measuring means tarnsforms the torque load measured on the electrical motor to a valve of pressure for the fluid forcing means. In the case of a shunt wound or permanent magnet D.C. motor the torque load is measured in terms of a current supplied to the motor.

The pressure signal means associated with the pump-up means may be of torque load type. Likewise, the pressure signal means may indicate the pressure of the system only while the fluid pumps out from the chamber and not during filling or pump-up. The pressure determined from the motor's torque load may be fed to a readout as well as to means for deactivating the electrical motor at a preselected high and/or low value of pressure. Blanking means may be included to interrupt the pressure measuring means during a portion of the piston cycle e.g.: filling and pump-up.

Thus, a novel and useful pump mechanism has been invented which minimizes the time duration of filling and pump-up of a pumping piston and maximizes the time duration of fluid flow at high pressures with a minimum pulsation.

It is therefore an object of the present invention to provide a low cost, reliable, and efficient pump mechanism for delivering fluids at high pressures in a pulseless state.

It is another object of the present invention to provide a pump mechanism compatible with liquid chromatographic systems including but not limited to packed columns.

It is yet another object of the present invention to provide a pump mechanism which will increase the time during which fluid is delivered to a receiving system and decreases the time of filling or refilling and pump-up prior to such delivery.

Another object of the present invention is to provide a pump mechanism which meters fluid flow under high pressures.

Still another object of the present invention is to provide a pump mechanism which measures pressure from the troque load on its motive means and feeds this value back to the motive means as a method of motive means speed control.

Another object of the present invention is to provide pressure signal means for an electric motor in combination with fluid forcing means in terms of the measurement of torque load on such an electric motor.

The invention possesses other objects and advantages especially as concerns particular features and characteristics thereof which will become apparent as the specification continues.

Various aspects of the present invention will evolve from the following detailed description of the preferred embodiment thereof which should be taken in conjunction with the accompanying drawings.

BRIEF DESCRIPTION OF THE DRAWINGS

FIG. 3 is a view taken along line 3—3 of FIG. 1.

FIG. 4 is a view taken along line 4—4 of FIG. 1.

FIG. 5 is a broken side view of the tachometer section shown in FIG. 4.

FIG. 6 is a block diagram of the electrical control means.

FIG. 9 is a block diagram of a preferred embodiment of the invention.

DETAILED DESCRIPTION OF THE PREFERRED EMBODIMENTS

Figure 1:
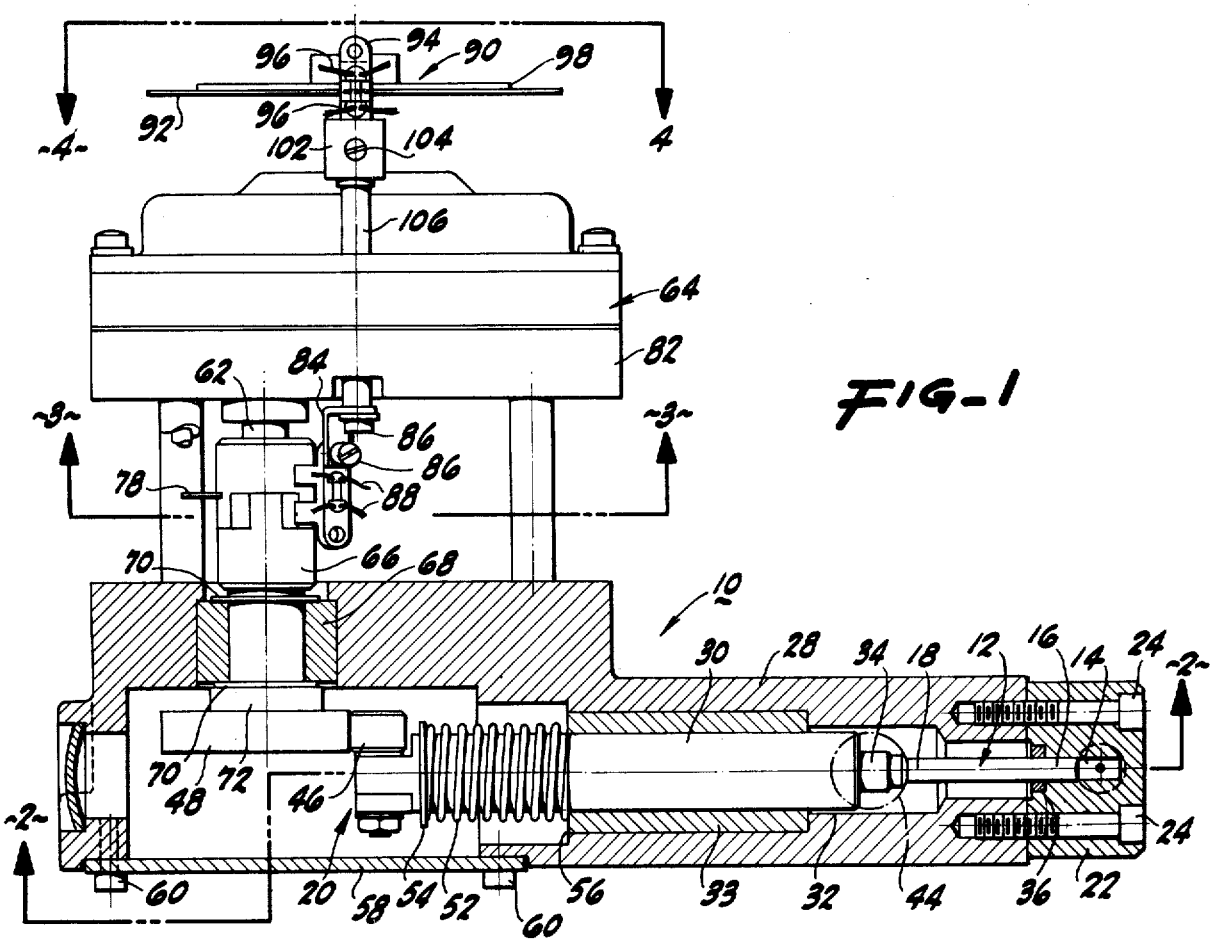
FIG. 1 is a top plan view of the mechanism with the piston section shown in section.

The pump mechanism of the present invention as a whole is indicated in the drawings by reference character 10 and includes as one of its elements a piston 12 which reciprocates within chamber 14. Piston first end portion 16 contacts the fluid traveling into and out of chamber 14, and piston second end portion 18 contacts motive means 20. Piston 12 moves back and forth within chamber 14 to fill and empty the chamber of fluid. As depicted in FIG. 1, the chamber fills when piston 12 moves from right to left.

Chamber housing 22 includes set screws 24 and studs 26 which engage pump body 28 to hold the chamber housing 22 in place. Plunger 30 rides within plunger barrel 32 and on bearing 33, and connects to piston second end portion 18 via ferrule 34. Seal 36 maintains the pressure integrity of chamber 14. Valve means 38, FIG. 2, includes an inlet check valve 40 and an outlet check valve 42 which threadingly engage chamber housing 22. Opening 44 permits the removal and inspection or repair of the connection of piston 12 to ferrule 34.

Plunger 30 terminates at the end opposite to piston second end portion 18 in a cam follower 46 which rolls or slides on cam surface 48 of cam 50. Cam support 74 further stabilizes cam follower 46. Spring means 52 bears on collar 54 of plunger 30 and shoulder 56 of pump body 28. Plate 58 and connecting bolts 60 permit access to the cam 50. Motive means further includes cam shaft 62 which turns by dint of the rotational force of electric motor 64, FIG. 1. The cam shaft 62 turns hub 66, within bearing 68 and seals 70, which in turn connects to hub 72 holding cam 50. Cam shaft 62 is reduced, by any conventinal means, to a slower speed, on the order of 50:1, than shaft 73 which turns without reduction on the opposite side of electric motor 64.

Figure 2:
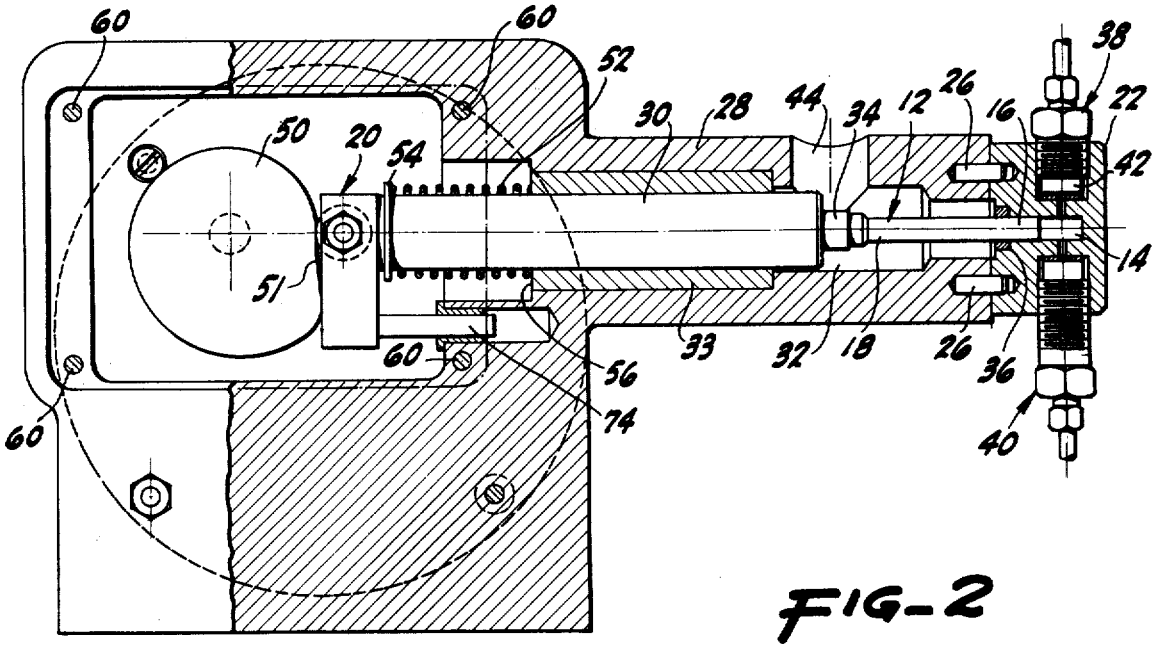
FIG. 2 is a view taken along line 2—2 of FIG. 1.

Control means 76, including detection means 77, shown in block diagram FIG. 6, interfaces with the mechanical elements of FIGS. 1 and 2 with a detector 75 such as photon intercepting flag 78 which turns with cam shaft 62 on hub 66, FIG. 3. Detector 75 further includes photon intercepting module 80 which fastens to motor housing 82 by means of bracket 84 and set screws 86. Terminals 88 relay the photon interruption of flag 78 to filling means 79. Similarly, shaft 73 terminates in tachometer means 90, FIGS. 1, 4, and 5, which has a graduated wheel 92 and an optical detector 94.

The wheel 92 is graduated into 360 transitions one for each degree of turn. Again terminals 88 transmit the light interruption in a series of electrical pulses. Disc 98 holds graduated wheel 92 onto shaft 74 with the aid of friction wheel 100. Optical detector 94 is supported by bracket 102 and set screws 104 in place. Appendage 106, fixed to motor housing 82 supports brackets 84, and 102 as desired.

Control means 76, FIG. 6 changes the speed of motive means 20 during the time period other than the time period when the chamber 14 is being emptied of fluid.

Turning to the block diagram, FIG. 6, normal or constant speed setting means 108 directs voltage to current sink converter 110 to pull a current proportional to constant speed setting means 108. Summing node 116 measures the error current between the current determined by the constant speed setting means 108 and the current from frequency charge pump 118 which produces a current proportional to the speed of motive means 20 measured by tachometer means 90. Summing amplifier 120, a high gain amplifier, delivers a servo error signal according to reference voltage 122 in comparison with the instantaneous error current at summing node 116. Servo gain and compensation means 124 provides feedback to summing node 116, but is a relatively small current when compared to the current from frequency charge pump 118.

Pulse width modulator generator driver 126 generates pulse width modulated signal which has a duty cycle proportional to the input error signal from summing amplifier 120. Pulse width modulator generator driver 126 then provides a changing voltage to motive means 20, which may be a D.C. motor. Thus, constant speed setting means 108 determined the speed of motive means 20 through a null circuit, including summing node 116, servogain and compensation means 124, summing amplifier 120, and reference voltage 122, and pulse width modulator generator driver 126.

After delivery of the fluid in chamber 14 by the emptying action of piston 12, at a selected normal or substantially constant speed, detection means 77 will acquire and signal the inception of the filling or refilling stroke of piston 12, and signal the termination of such filling stroke. As previously discussed, such detection means 77 may be accomplished in the preferred embodiment by a photon intercepting flag 78 interrupting module 80, during the filling stroke of piston 12. Likewise, detection means 77 may take the form of a pulsing tachometer coupled with a triggered or resetting digital counter to sum pulses therefrom, to indicate the period of the filling stroke of piston 12. For example, in the present embodiment, the onset of the filling of chamber 14, where motive means 20 includes a D.C. motor, reverses the load upon such motor because of the negative slope 51 on cam 50. The sudden drop in motor current may be detected and employed to start a digital counter. This indication of the beginning of filling stroke of piston 12 may be accomplished by other timing or shaft rotational measuring devices known to persons of ordinary skill in this art. The digital counter would determine the angular duration of the filling period. An analog integrator could also be employed for this purpose, by integrating a tachometer signal and producing an output proportional to angular duration for the filling period. The digital count would be compared to a standard count representing the filling movement of piston 12. The analog integrator, on the other hand, would be compared to a fixed or reference voltage representing the end of the piston's filling stroke. A typical value of the angular duration of the filling or refilling stroke of piston 12 is about 50 degrees.

Filling amplifier 128 coupled to a detector 75 senses the beginning of the filling stroke of piston 12 and signals and activates first switch means 114 via "OR" gate 130 and second switch means 132 directly. First switch means 114 in conjunction with constant speed decoupling means 112 effectively bypasses the voltage to current sink converter 110 and pump-up speed control 152 from summing node 116. Thus, filling speed control means 134 determines the speed of motive means 20 while the piston 12 moves through its filling or refilling stroke. Filling speed control means 134 increases the speed of motive means 20 in most cases at a rate commensurate with such considerations as, the cavitation and degassing characteristics of the fluid, liquid, solvent, or the like, being pumped by mechanism 10.

Furthermore, the speed of valve means 38, as well as the hydraulic geometry of the mechanism 10 must be considered as a limiting factor for pumped liquids. At very fast normal speeds, the motive means may slow during filling because of these factors. This is especially true of low boiling point solvents such as pentane, ethyl ether and the like.

The inception of filling speed-up by filling means 79 also sets charge integrator 136 to a very low value and it remains there during the refilling stroke of piston 12. The termination of the refilling stroke of piston, 12 signaled by detection means 77, deactivates switch means 114 and 132. However, fluid is not delivered until the emptying stroke of piston 12 overcomes the back pressure on outlet check valve 42 and piston seal compressibility, liquid compressibility, chamber deformation and like phenomena, generally referred to as "compliance". For a typical liquid chromatographic system piston 12 must travel along its emptying strokes approximately seven (7) micro-liters for a 140 kilogram/square centimeter back pressure, with a generally linear increase thereafter. This period in piston 12's reciprocations is called "pump-up".

At the beginning of pump-up, pump-up means 138 changes the speed of motive means 20. Pump-up means encompasses pump-up gain means 142 which includes tachometer means 90 measuring the axial rotational rate of shaft 73 and transforming this measurement of axial rotation into a pulse signal received by frequency charge pump 118. Gain means 144 which may be coupled with frequency charge pump 118 adjusts the amplitude of the pulse signal from the tachometer means 90 or the frequency charge pump 118 and transmits the amplitude adjusted pulse signal to charge integrator 136. A ramp signal results which feeds into comparitor means 140. Such a ramp signal is proportional to shaft 73 rotation, cam 50 rotation or the linear displacement of piston 12.

Comparitor means 140 utilizes comparitor 146 which also receives a back pressure signal from pressure measuring means 148. The output of comparitor 146 travels through "and" gate 150 while the charge integrator 136 output increases but is less than the back pressure signal, i.e.: during the pump-up period. The comparitor 146 outputs adds an additional current to ground from summing node 116 via pump-up speed control means 152. The "step-up" of pump-up speed control increases the speed of motive means 20 until the ramp signal substantially equals the back pressure measuring from pressure signal means 148. This, of course, means that the piston 12 has generated enough fluid pressure to overcome the back pressure on outlet check valve 42, provided that gain means 144 has been properly adjusted, and the pump mechanism 10 reverts to its normal or constant filling speed. Integrator 136 stays high until the next refilling cycle. There is essentially an instantaneous switch from filling speed change to pump-up speed change to minimize or eliminate any slack when fluid is not being delivered. Pump-up speed control isolator 154 prevents activation of pump-up speed control during normal operation.

Pump-up gain means 142 may increase or decrease the pump-up period measured in piston linear displacement or in the angular rotation of the shaft 73 for a given back pressure signal. Gain means 144 specifically increases or decreases the slope of the ramp signal to this end. Changing the pump-up period is necessary to correct for different liquid solvent viscosities, chromatographic column resistance and other factors affecting flow rate.

Since the time span of filling and pump-up are finite, the desired flow rate determined at the normal speed setting means 108 may not equal the actual average flow rate from the outlet of chamber 14. Thus "pump-up" may exceed the time when outlet check valve 42 opens in some cases. Also, the back pressure on check valve 42 may drop during filling and "pump-up" producing a slight pulse in the fluid flow. Gain means 144 also reduces this pulse by matching the flow rate setting with the acutal flow rate delivered by mechanism 10.

The preferred embodiment is deemed to be drawn to a pressure signal device alone or in combination with the heretofore described pump mechanism 10. Pressure measuring means 148 measured the torque on motive means 20 and transforms the same into a measurement of back pressure associated with a fluid forcing means such as piston 12 and chamber 14. Motive means 20 may include a direct current electric motor in which case, the current delivered to the motor would be proportional to the torque load on the motor and therefore would be transformable into a measurement of back pressure by pressure measuring means 148.

Means 158 for deactivating the motive means 20 at selected back pressure valves, either high or low or both, may take the form of a high low pressure detector 160 with a limit indicator 162. High pressure limiting means 164 may be provided with hysteresis means 164 for reactivating the motive means 20 when the back pressure again falls within the selected working range.

Drive detector means 168 and time delay means 170 as well as comparitor output 146 through inverter 172 and "and" gate 150 feed to "and" gate 174. The output of "and" gate 174 and the output of high low pressure detector 160 travel through "or" gate 176 and inverter 178 to deactivate pressure measuring means, and form blanking means 180. This prevents the measurement of pressure during filling, pump-up and a coasting down period after pump-up for a set time period, provided by time delay means 170.

Figure 8:
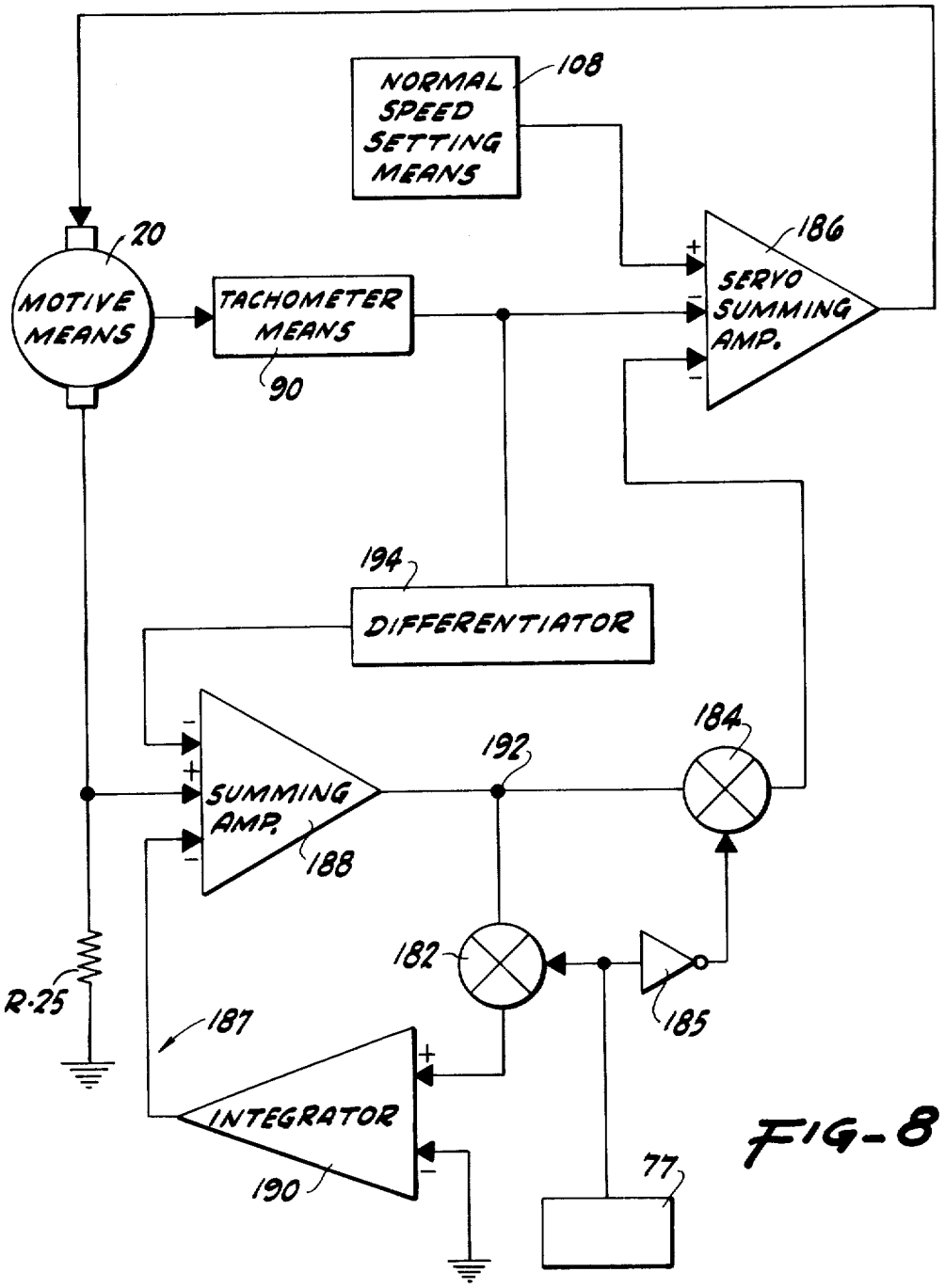
FIG. 8 is a block diagram of a preferred embodiment of the invention.

Block diagram, FIG. 8, shows a variation of the invention 10, in particular, control means 76. Detection means 77 could signal the inception of the chamber filling stroke of piston 12 and may take the form of the photon interruption flag 78 and associated elements and other equipment structures previously described. However, detection means 77 is shown as signaling the inception of the pump out of fluid during the normal pumping period of piston 12. At this time switch means 182 is "on" and switch means 184 is "off". Switch means 182 and 184 may take the form of analog transmission gates. At this point, the torque load on motive means 20 is constant and proportional to the back pressure of the liquid being pumped. Normal or constant speed setting means 108, previously delineated, determines the speed of motive means 20 via servo summing amplifier 186 which produces an amplified error signal from the tachometer 90 and normal speed setting means 108 inputs.

During normal flow, a negative feedback loop 187, consisting of summing amplifier 188, integrator 190 and switch means 182, produces an average torque error signal at node 192 of zero. Summing amplifier 188 compares the instantaneous motor current from sensing resistor R-25, which is proportional to torque when motive means 20 in a D.C. motor, to the output of integrator 190. Integrator 190, in turn, receives the torque error signal of the negative feedback loop 187 and an input from ground.

In other words, the output signal of integrator 190 equals the average signal across the current sensing resistor R-25, during normal pumping.

At the inception of the filling period detection means 77 cause switch means 182 to turn "off" breaking the negative feedback loop 187, and freezing the output of integrator 190, to its last value. Switch means 184 is turned "on" via inverter 185. During filling, the torque on motive means 20 greatly reduces such that the torque signal input to summing amplifier 188 is less than the output signal of integrator 190. The torque error signal i.e.: summing amplifier 188 output, travels through switch means 184 to servo summing amplifier 186. The addition of the torque error signal, thereto, will cause motive means 20 to run at maximum speed because of the large amplified error signal received from servo summing amplifier 186.

At the end of refill, and the beginning of pump-up, the load on motive means 20 increases and the torque error signal begins to drop. As the load continues to increase the torque error signal further decreases until motive means 20 begins to decrease. By the end of the pump-up period, the torque error signal decreases to zero and has no further effect on servo summing amplifier 186. Therefore, motive means 20 returns to the normal speed for pumping the fluid. Detection means 77 again signals the inception of the normal pumping period which turns switch means 184 "off" and switch means 182 "on".

Differentiator 194 produces a signal proportional to the acceleration of motive means 20. This acceleration signal is subtracted from the torque signal of R-25. The net result is a true torque error signal to servo amplifier 186 during filling and pump-up. As may be surmized the embodiment of FIG. 8 does not require a compressibility adjustment necessitating gain means 144 in the prior embodiment.

FIG. 9 depicts another embodiment of the present invention where the actual pressure in the piston chamber 14 is sensed by a pressure transducer 196 instead of using motor torque as the pressure sensor. The null loop 187 formed by summing amplifier 188 and integrator 190 tracks the piston chamber pressure when switch 182 is "on". Switch 182 turns "on" by the action of sensor 77 during the guaranteed delivery stroke of piston 12, that is to say, after the pump-up period. Thus, the guaranteed delivery period necessarily excludes the initial period of the piston's forward stroke which produces pressure to overcome the back pressure on the system.

The guaranteed delivery period would exclude, therefore, sufficient piston displacement to allow pressurization of chamber 14 to the highest operating pressure of the pump i.e.: 6,000 to 10,000 P.S.I.

Switches 182 and 184 are driven out of phase. When switch 182 is on, the action of null loop tends to minimize or zero-out signal 192. Null circuit 187 servos to the average value of pressure signal 198, since amplifier 188 defines the difference between the actual chamber pressure signal 198, and the output of integrator 190 and the null loop 187 defines the average difference to be zero. When switch 182 turns off (during refill and pump-up) there is no input to the integrator 190. Output of integrator 190 remains unchanged in a hold state. At this time, output of integrator 190 is equal to the previous average piston chamber pressure during the delivery stroke.

A velocity servo control loop consisting of summing amplifier 186, setting means 108, motive means 20 and tachometer means 90 regulates the speed of motive means 20 to whatever value is set into normal speed setting means 108. The configuration of cam 50 insures a metered flow rate of fluid from chamber 14 during the delivery stroke of piston 12.

At the end of the delivery stroke of piston 12 detection means 77 opens switch 182 which holds the average pressure signal, i.e. the output of integrator 190. Switch 184 closes which connects the pressure error signal 192 to the servo summing amplifier 186. During refill and pump-up pressure error 192 is large and negative. Pressure error signal 192 feeds into a negative input on servo summing amplifier 186. This negative error signal increases the speed of motive means 20 to overcome the pressure error. As a net result, refill and repressurization occur in the minimum possible time, dependent on the maximum attainable speed of motive means 20. Pressure error signal 192 approaches zero when the piston chamber pressure equals the previously remembered value. This allows the velocity of motive means 20 to return to its normal speed and, assure the correct flow rate therefrom, as defined by normal speed setting means 108. By this embodiment, the time during which piston 12 is not delivering is minimized. Flow rate is concurrently corrected for solvent and system compressibility. Thus, the need for a compressibility compensation adjustment is eliminated. Although short duration pulses ensue they are easily filtered on the outlet of the pump chamber 14, by a hydraulic pressure filter, well known in the art.

Figure 7:
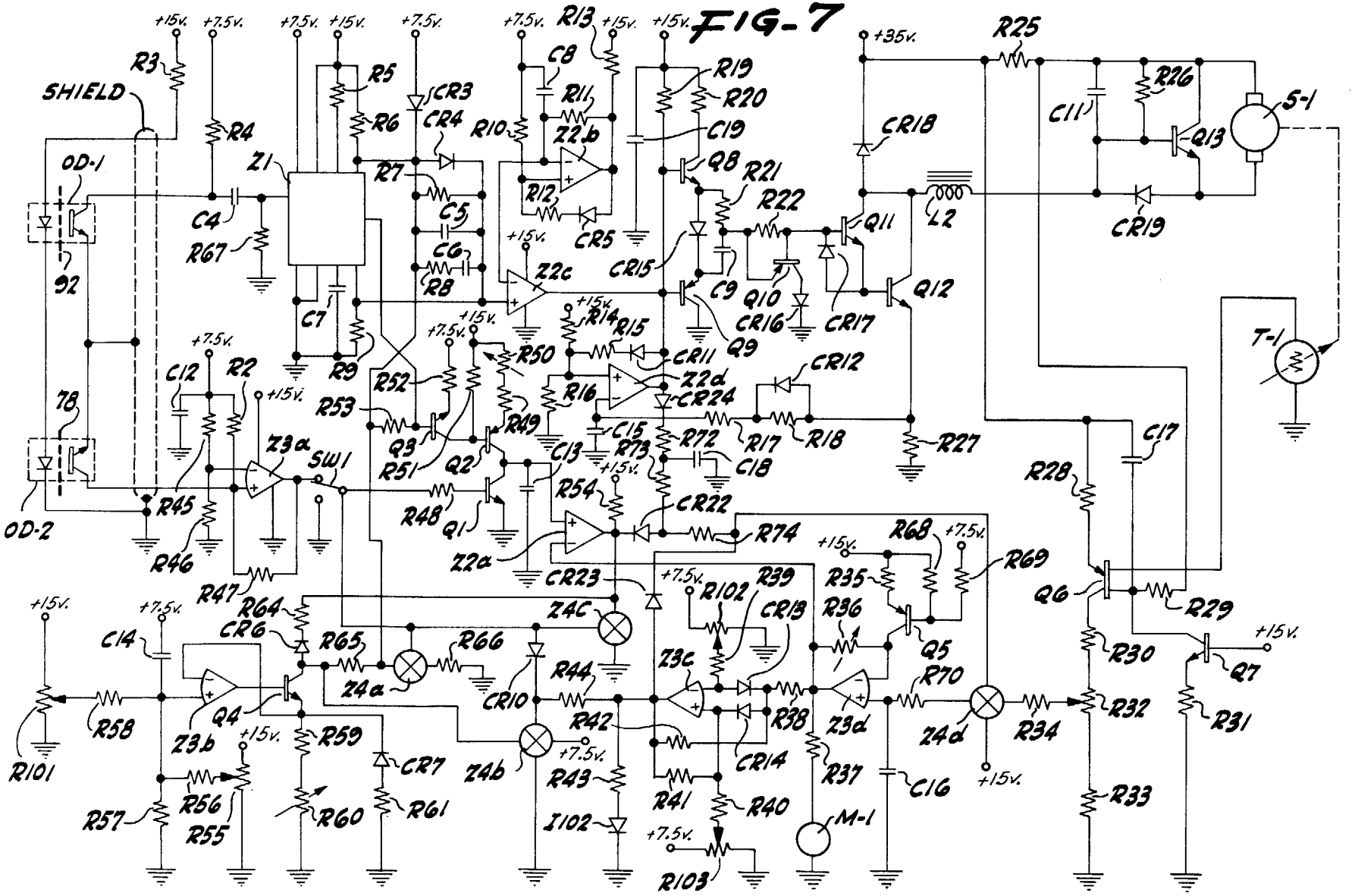
FIG. 7 is an electrical schematic diagram of a preferred embodiment of the invention.

Now considering the schematic circuit drawing FIG. 7 the following Table I is a list of the elements found in the circuit with the model number of values used in the embodiment shown in FIG. 6.

TABLE I

| TABLE OF ELEMENTS | |
|---|---|
| INTEGRATED CIRCUITS | |
| Z - 1 National Semi-conductor LM 2907N | |
| Z - 2 National Semi-conductor LM 339N | |
| Z - 3 National Semi-conductor LM 324N | |
| Z - 4 R.C.A. CD 4066 AE (QUAD BILATERAL SWITCH) | |
| DIODES | |
| CR 3 through CR 17, CR 22, CR 23, CR 24 | IN 914 |
| CR 18, CR 19 | MR 850 |
| TRANSISTORS | |
| Q - 3, Q - 4 | 2N 930 |
| Q - 11 | 2N 5189 |
| Q - 9, Q - 10 | MPS 3638A |
| Q - 1, Q - 8, Q - 7, | MPS 6531 |

TABLE I-continued

| TABLE OF ELEMENTS | |
|---|---|
| Q - 13 | R.C.A. 2N6386 |
| Q - 2, Q - 5, Q - 6 | M.P.S. 4355 |
| Q - 12 | R.C.A. 40375 |
| CAPACITORS | |
| C - 16, C - 19 | 15 uf, 20 v |
| C - 4, C - 9, C - 12, C - 17, C - 18 | 0.1 uf, 50 v |
| C - 5 | 0.02 uf, 100 v (± 20%) |
| C - 6, C - 13 | 2.2 uf 50 v (ceramic) |
| C - 7 | C20 Pf ± 2.5% |
| C - 8 | 0.001 uf ± 20% |
| C - 11 | 100 uf, 50 v (electrolytic). |
| C - 14 | 1.0 uf |
| C - 15 | 0.01 uf |
| RESISTORS | |
| R - 25, R - 27 | 0.3 ohms, 2 w |
| R - 26 | 68 ohms, 2 w |
| R - 20 | 47 ohms, ¼ w |
| R - 22 | 68 ohms, ¼ w |
| R - 17 | 470 ohms, ¼ w |
| R - 2, R - 21, R - 45, R - 73 | 1 Kohm, ¼w |
| R - 28, R - 18 | 1.5 Kohm, ¼ w |
| R - 5, R - 14 | 2.2 Kohms, ¼ w |
| R - 29, R - 43 | 3.3 Kohms, ¼ w |
| R - 16 | 3.9 Kohms, 1.4 w |
| R - 9, R - 41, R - 49 | 4.7 Kohms, ¼ w |
| R - 13, R - 33, R - 38, R - 52, R - 54, R - 65, R - 68, R - 69 | 10 Kohms, ¼ w |
| R - 51, R - 53 | 15 Kohms, ¼ w |
| R - 12, R - 4, R - 67 | 22 Kohms, ¼ w |
| R - 11, R - 44, R - 48, R - 74. | 30 Kohms, ¼ w |
| R - 10, R - 30 | 39 Kohms, ¼ w |
| R - 15, R - 46 | 47 Kohms, ¼ w |
| R - 64, R - 8, R - 34, R - 70, R - 72 | 100 Kohms, ¼ w |
| R - 31 | 120 Kohms, ¼ w |
| R - 14 | 200 Kohms, ¼ w |
| R - 39, R - 40 | 220 Kohms, ¼ w |
| R - 35 | 150 Kohms, ¼ w |
| R - 42 | 390 Kohms, ¼ w |
| R - 47 | 420 Kohms, ¼ w |
| R - 7, R - 6, R - 71 | 10 Mohms, ¼ w |
| R - 37 | 7.5 Kohms, ¼ w |
| R - 58 | 499 Kohms, ¼ w |
| R - 59 | 12.1 Kohms, ¼ w |
| R - 57 | 42.4 Kohms, ¼ w |
| R - 56 | 27 Mohms, ¼ w |
| R - 3 | 560 ohms, ½ w |
| R - 41 | 4.7 Mohms, ¼ w |
| R - 32, R - 55, R - 60 | 10 Kohms, (trimpot) |
| R - 36 | 100 Kohms, (trimpot) |
| R - 50 | 10 Kohms, (trimpot) |
| R - 66 | 75 Kohms, ¼ w |
| R - 101 | 10K, ratio 100/10.0 (Digital Potentiometer) |
| R - 102 | 10 Kohms |
| R - 103 | 10 Kohms. |
| MISCELLANEOUS | |
| OD - 1, OD - 2 | Optical Detector - G.E. photon coupled interrupter Module # 13A1 |
| T - 1 | Thermister 250 Kohms at 25° C., 50 Kohms at 70° C. |
| S - 1 | Electrical motor, permanent magnet motor, 1/30 H.P., 12 v D.C., amps. 0–3000 RPMS, 50:1 gear ratio. |
| M - 1 | Meter, 0–1 milli amps (full scale) |
| I - 102 | Light emitting diode #HP5082 - 4940 - 44403 |
| SW - 1 | Single pole single throw, slider switch. |
| L - 2 | 300 U Henry, 3 amps. |

The power inputs are denoted by a small circle with the approximate voltage value in the vicinity of the power input, in volts D.C.

Normal speed setting means 108 may take the specific embodiment shown where R-101, a variable resistor combines with R-58 and C-14 which act as a low pass filter that averages the alternating current variations from a direct current signal ie: a pulse width modulated signal. This is especially true when the signal comes from a remote programer not shown. R-55, R-56, R-6, and R-57 inject a zero offset to normal speed setting means 108. Therefore, the R-55 zero setting becomes a true zero.

Voltage to current sink converter 110 corresponds to operational amplifier Z-3-b in whose outputs enter Q-4, a high gain transistor. Q-4's collector pulls current through R-59 and R-60 to match the inputs to amplifier Z-3-b. It should be noted R-60 is a variable resistor which may be used as a calibration control for the voltage to current sink converter. R-61 and CR-7 combine to correct for non-linearity of the normal speed setting means 108 and its flow rate determination because of the rilling means 79. This is especially useful at low flow rates where the distortion is greatest.

R-65 serves as the normal speed decoupling means 112. It has equal voltage on the order of 7.5 volts on either side for decoupling normal speed setting means 108 and pump-up means 138 when Z-4-b, which is first switch means 114, is turned "on" by filling means 79.

The summing node 116 leads directly into Z-1 which corresponds to frequency charge pump 118, a frequency to current converter with frequency doubling characteristics. Z-1 also includes summing amplifier 120, a high gain amplifier.

Tachometer means 90, OD-1, sends to Z-1, a pulsating current whose frequency is proportional to the speed of motive means 20. R-4 serves as a pull-up load resistor while C-4 acts as a decoupling capacitor to block the D.C. component of the A.C. signal coming from the chopping action of OD-1. The A.C. signal passes to Z-1 and is referenced to ground through R-67. C-7 determines the quantity of charge delivered, for each axis crossing of the A.C. signal, by the frequency charge pump 118; hence C-7 determines the gain of the charge pump. R-9 is a pull-down resistor from the output of the summing amplifier 120 within Z-1.

Frequency charge pump 118 passes current from Z-1 to R-53 and finally to summing node 116. Likewise, the output of summing amplifier 120 with the aid of pull-down resistor R-9 produces a very small negative feedback current through R-7 to summing node 116. CR 3, and CR 4 are used for clamping limits on the error signal at the summing node 116. In this case, the output of the summing amplifier 120 and summing node 116 can not go below 7 volts. Thus the recovery time of the summing amplifier 120 is reduced if it becomes overloaded.

C-5, R-8, and C-6 determine the high frequency gain rolloff characteristics. ie: the values have been predetermined such that the whole servo loop does not oscillate and has proper damping characteristics as well as maximum response time R-5 provides a pull-up current to a portion of the summing amplifier 120 within Z-1. R-6 injects a small positive current into summing node 116 which adjusts R-55 to a true zero value, as previously discussed.

Summing amplifier 120 also feeds Z-2-C which comprises a part of the generator section of pulse width modulator generator driver 126. The error signal from summing amplifier 120 in Z-1 is compared to a triangular wave signal from the triangular wave from the generator composed of Z-2-b, in conjunction with passive components C-8, R-11, R-13, R-10, R-12, and CR 5. The resulting output of Z-2-C is a pulse width modulated signal which passes to the driver section of generator drive 126. The duty cycle of the pulse width modulated signal is directly proportional to the error signal from amplifier 120.

Q-8, Q-9, Q-10 and Q-11 drive Q-12 "on" and "off" synchronously at a very fast rate. R-19 is a pull-up resistor for Z-2-C while C-19 filters the power supplied, thereto. R-20 functions to limit the peak current through Q-8. When Q-8 goes "on", Q-9 turns "off", thus Q-8 and Q-9 are complimentary. The pulse width modulated signal, having a frequency of about 25 Kilohertz, is initially high and positive, flowing current through CR-15, and C-9, R-21, R-22, Q-10, and to the base of Q-11.

Q-10 bypass to ground, through CR-16, any excess current exceeding approximately 10 milliamperes coming from Q-8. The current through R-22, the portion not bypassed, passes to the base of Q-11 turning it off. The limiting action of Q-10 prevents Q-11 from being overdriven on initial turn on, allowing it to turn off more quickly. After the charge-up of C-9, R-21 limits the drive current through Q-8 to approximately 10 milliamperes such that Q-10 bypasses essentially no current to ground after the charge up period of C-9, Q-12 turns on within a time period of 200 nanoseconds from the beginning of the turn on sequence causing the voltage on its collector to reach a low value. When the pulse width modulated signal goes low, Q-9 turns "on" and Q-8 turns "off" allowing the voltage at the emitter of Q-9 (top of C-9) to go low. C-9 supplies a source of negative bias in order to sink large currents very rapidly from the bases of Q-11 and Q-12 through CR-17. This turns Q-11 and Q-12 "off" very rapidly permitting the voltage on the collectors of Q-11 and Q-12 to go high. This "on"-"off", high/low sequence takes place at a relatively high frequency of 25 kilohertz which eliminates any audio sounds eminating from motive means 20. The need of a large heat sink to dissipate heat from Q-12 is eliminated because of high/low switching which takes place in 200 nanoseconds, as heretofore described.

The embodiment described also performs current limiting through Q-12 using current sensing resistor R-27 and Z-2-d and its associated circuiting. Z-2-d is a comparitor which compares a reference voltage, established by R-14, R-15, and R-16, and a signal voltage developed across C-15. Such a signal voltage averages the voltage drop across the current sensing resistor R-27, with a weighted dual time constant originating from R-17, R-18, and CR-12. For instance, when the voltage drop across R-27 exceeds the voltage across C-15, CR-12 is forward biased so that R-17 determines the time constant with C-15. A typical value would be 4.7 microseconds in this case. On the other hand, when the voltage drop across R-27 is less than the voltage across C-15, CR-12 is reversed biased so that R-17 and R-18 determines the time constant with C-15 e.g.: 20 microseconds. When the signal voltage exceeds the reference voltage in comparitor Z-2-d, the output of comparitor Z-2-d overrides the pulse width modulated signal from Z-2-c, thereby shutting down the driver section of 126. R-15 drops the reference voltage to a low level which guarantees the driver wall remain "off" for about 30 microseconds. When the signal from C-15 is discharged below the lowered reference signal, Z-2-c is re-enabled to reactivate the driver section of 126. The "on-off" action of this current limiting occurs at an ultrasonic frequency of about 25 kilohertz again, preventing disturbing sympathetic sonic frequencies from arising. Current limiting may occur at a value of about 4 amps measured through R-27.

L-2 and C 11, a low pass filter, react slowly to current changes from the driver section of 126, and thereby convert the pulse width modulated signal therefrom to a D.C. signal supplied to S-1. R-26, Q-13, and CR 19 form a dynamic break to prevent overspeeding of S-1. In other words, when CR 19 is forward biased Q-13 is "off" and the L-2 and C-11 combination runs S-1. In other words, when CR 19 is forward biased, Q-13 is "off" and the L-2 and C-11 combination runs S-1. However, if the D.C. voltage generated by motor S-1 exceeds the D.C. supplied across C-11, CR-19 will reverse bias and Q-13 goes "on" thereby short circuiting and braking S-1. The CR 18 diode clamps the voltage on the collectors of Q-11 and Q-12 to the 35 volt source when Q-12 is turned off.

Pressure measuring means 148 employs current sensing resistor R-25 which effectively measures the current load on S-1. This current load is proportional to the torque load on S-1 which is proportional to the back pressure exerted on mechanism 10, which may include fluid forcing means as previously described in FIGS. 1 and 2. A motor current sensing common emitter amplifier is embodied by Q-6 and accompanying resistors R-28, R-30, R-32, and R-33. Q-7 and R-31 form a current biasing network for Q-6. C-17 and R-29 filter high frequency noise from the current amplification at this point.

T-1 reduces the gain of the pressur sensing amplifier Q-6, as the torque constant of S-1 decreases with increased temperature.

R-30 serves to limit the potential across the R-32 pot to 15 volts, consequently R-32 serves as a span adjustment for meter M-1, which will be hereinafter discussed.

Signal conditioning of the signal from R-32 is provided by low pass filter R-34, R-70, and C-16. This R-C element may have a time constant of about 3 seconds. Z-4-D is a switch that maintains the charge on C-16 when in the "off" position. The charge on C-16 represents the average voltage at R-32 i.e.: the output of the motor current sense amplifier Z-3-d is a non-inverting unity gain amplifier which subtracts an adjustable offset due to R-36. The output of Z-3-d equals zero volts, by the adjustment of R-36; no back pressure is found on piston 12 at this point. Meter M-1 and R-37 provide a pressure readout.

Switch Z-4-d will turn off during filling, pump-up, and a time period following pump-up where the piston coasts down to a normal speed. This aspect of the invention shown of FIG. 6 as blanking means will be fully explained hereafter.

High/low pressure detector 160 includes an upper limit voltage setting means R-102 and a lower limit voltage setting means R-103. Z-3-C compares the upper limit to lower limit through resistors R-39, R-40, R-41 and R-42, CR-13 and CR 14 are forward biased between upper limit pot R-102 and lower limit pot R-103. The output of Z-3-C remains low when the upper limit input is greater than the lower limit input, and the pressure voltage at the Z-3-d output is within such limits. When the output of Z-3-d exceeds the upper limit, CR 13 reverse biases causing the output of Z-3-C to go high, activating first switching means 114. R-65 becomes shorted stopping motive means 20. When the pressure on the system reduces, R-38, R-40, R-41 and R-42, comprising hysteresis means of high pressure limiting means 164, restart motive means 20. When the output of Z-3-d goes below limit voltage, CR 14 reverse biaser causing Z-3-c output to go high shutting off motor S-1. R-103 is then adjusted to restart motor S-1. Limit indicator 16 is formed by R-43 and light emitting diode I-102.

Filling means 79 includes detection means 77, which encompasses photon intercepting flag 78 and module 80. OD-2 represents flag 78 and module 80. Z-3-A and R-47, a noise suppressor, would function as filing amplifier 128. SW-1 is a switch to disable detection means 77. The generated signal from OD-2 in conjunction with filling amplifier 128 turns on Z-4-B, first switching means 114, through CR 10 and R-44 which compose "OR" gate 130. Thus, R-66 determines the speed of S-1 during filling, since R-65 has equal potential on either side. Also, the output of Z-3-A enters Q-1, through current limiting resistor R-48, which sets C-13 to a low value (i.e.: zero). C-13 would be an embodiment of charge integrator 136. The output of Z-3-A controls Z-4-C, which is turned "on" by the flag 78 intercepting the photon beam in module 80. Z-4-C and Z-2-A serve as "and" gate 150 and inverter 172. CR 22 and R-73 form "and" gate 174. CR 23 and R-74 comprise "OR" gate 176 and inverter 178. R-54 is a passive pull-up resistor to maintain a positive voltage on Z-4-C when Z-2-A and Z-4-C are off. Thus, a blanking signal to Z-4-D results during fast refill, deactivating pressure measuring means 148, as previously discussed. When such a blanking signal is received by Z-4-D holding means, C-16 will hold the value of the current sense amplifier previously described in conjunction with Q-6 at R-32. The result will be a steady pressure reading on pressure measuring means 148 during the refill and pump-up period of the cycle of piston 12.

As soon as the flag 78 signals the end of the filling period, pump-up will begin. A ramp signal will be produced and sent to Z-2-A which corresponds to comparitor 146. A second signal from Z-3-D indicates the back pressure on the mechanism 10. The advent of pump-up removes R-66 from motor speed determination and substitutes the R-64 and R-65 combination. In other words, the preferred embodiment adds a step to the normal speed setting during pump-up. Also, Z-4-D receives another blanking signal via CR 22, and reacts as during the filling sequence. After pump-up has been completed C-18 will continue the blanking signal for a set time period to prevent pressure measurement during the "coasting down" of motor S-1 to the normal speed setting and normal flow rate delivery.

The ramp signal arriving at Z-2-A is generated by Q-2 and Q-3 and resistors R-49, R-50, and R-52, which form a current mirror that tracks the current flow from the Z-1 frequency charge pump, flowing through R-53. These combined elements form pump-up gain means 142. R-50 corresponds to gain means 144 for the amplitude adjustment of the pulse signal of frequency charge pump 118 of Z-1.

During high or low limiting CR-23 gurantees that switch Z-4-d is on, preventing "latch-up" of high pressure limiting means 160. Thus, high pressure limiting means resets automatically.

While in the foregoing specification embodiments of the invention have been set forth in considerable detail for purposes of making a complete disclosure of the invention, it will be apparent to those skilled in the art that numerous changes may be made in such details without departing from the spirit and principles of the invention.

What is claimed is:

1. A liquid chromatograhy pump comprising:

a. piston, at least a portion of which is reciprocative within a chamber having a fluid inlet and a fluid outlet, said piston having a first end portion and a second end portion, said first end portion contacting the fluid, said piston being capable of filling and emptying said chamber;

b. motive means for reciprocating said piston within said chamber at a selected substantially constant speed, said substantially constant speed determined by constant speed setting means for fixing said motive means at a substantially constant speed, said motive means contacting said second end portion of said piston;

c. valve means for permitting the filling and emptying of said chamber coordinated with the pressure exerted by said piston within said chamber, said piston, motive means, and valve means cooperating to produce a fluid flow during a particular time period, from said piston chamber relative to said selected substantially constant speed;

d. control means for changing the speed of said motive means at a preselected portion of the time period of said reciprocation of said piston within said chamber, said control means including means for changing the speed of said motive means at the termination of the chamber emptying stroke of said piston, and returning said motive means to said predetermined constant speed after a certain distance of travel of said piston during its subsequent emptying stroke, said motive means speed changing means including pressure measuring means for measuring and signaling the pressure at said piston chamber; and detection means for detecting and signaling the termination of said chamber emptying stroke of said piston, said motive means speed changing means activated upon receipt of said chamber emptying stroke termination signal from said detection means, said motive means returning to said substantially constant speed upon receipt of said pressure signal from said pressure measuring means.

2. The liquid chromatographic pump of claim 1 in which said pressure measuring means comprises a pressure transducer communicating with said piston chamber.

3. A liquid chromatography pump for delivering fluid against a back pressure comprising:

a. piston, at least a portion of which is reciprocative within a chamber having a fluid inlet and fluid outlet said piston having a first end portion and a second end portion, said first end portion contacting the fluid, said piston being capable of filling and emptying said chamber;

b. motive means for reciprocating said piston within said chamber at a selected substantially constant speed, said substantially constant speed determined by constant speed setting means for setting said motive means at a substantially constant speed, said motive means contacting said second end portion of said piston;

c. valve means for permitting and filling and emptying of said chamber coordinated with the pressure exerted by said piston within said chamber; said piston, motive means and valve means cooperating to produce a time duration of fluid flow from said chamber relative to said selected substantially constant speed;

d. control means for changing the speed of said motive means at a preselected portion of the time period of said reciprocation of said piston within said chamber, said control means comprising detection means for signaling the inception and termination of the emptying of said chamber by said piston; pressure measuring means for measuring and signaling the pressure at said piston chamber; summing amplifier producing an error signal; integrator receiving said error signal from said summing amplifier and a signal from ground, said summing amplifier and a signal from ground, said summing amplifier receiving as inputs said pressure signal and the output signal of said integrator, tachometer means producing a signal proportional to the speed of said motive means said constant speed setting means producing a reference signal corresponding to a desired speed of said motive means; and servo summing amplifier, said error signal from said summing amplifier, said tachometer means signal and said normal speed setting means signal serving as inputs to said servo summing amplifier, said servo summing amplifier producing an amplified error signal to said motive means.

4. The liquid chromatographic pump of claim 3 in which said pressure measuring means comprises a pressure transducer communicating with said piston chamber.

*5. A fluid pump mechanism for delivering fluid against a back pressure comprising:*

*a piston movable within a chamber for drawing fluid into the chamber during a chamber filling interval, pressurizing the fluid during a pressurizing interval and delivering the pressurized fluid from the chamber during a delivery interval of piston movement;*

*means for moving the piston at a predetermined rate during delivery of the pressurized fluid;*

*means including a pressure transducer communicating with the chamber for generating a signal having a value related to the pressure of fluid in the chamber;*

*means for storing the value of the signal generated during a delivery interval;*

*means for comparing a present value of the signal during the chamber pressurizing interval with the stored value; and*

*means for changing the rate of piston movement during at least a portion of the chamber pressurizing interval to a rate exceeding the predetermined rate by an amount related to any difference between said present and stored values.*

*6. The mechanism of claim 5 further including means for changing the rate of piston movement during the chamber filling interval to a rate exceeding the predetermined rate.*

* * * * *